United States Patent
Szardenings et al.

(10) Patent No.: US 10,011,825 B2
(45) Date of Patent: Jul. 3, 2018

(54) METHOD FOR ACTIVATING A SURFACE BY INCREASING THE HYDROPHILICITY AND/OR FOR BINDING TARGET STRUCTURES

(71) Applicant: Fraunhofer-Gesellschaft Zur Foerderung Der Angewandten Forschung E.V., Munich (DE)

(72) Inventors: Michael Szardenings, Leipzig (DE); Klaus Rischka, Tostedt (DE); Ingo Grunwald, Lilienthal (DE); Annika Eisenschmidt, Heidelberg (DE)

(73) Assignee: FRAUNHOFER-GESELLSCHAFT ZUR FOERDERUNG DER AGNEWANDTEN FORSCHUNG E.V., Munich (DE)

( * ) Notice: Subject to any disclaimer, the term of this patent is extended or adjusted under 35 U.S.C. 154(b) by 0 days.

(21) Appl. No.: 14/407,215

(22) PCT Filed: Jun. 14, 2013

(86) PCT No.: PCT/EP2013/062453
§ 371 (c)(1),
(2) Date: Dec. 11, 2014

(87) PCT Pub. No.: WO2013/186392
PCT Pub. Date: Dec. 19, 2013

(65) Prior Publication Data
US 2015/0159150 A1    Jun. 11, 2015

Related U.S. Application Data

(60) Provisional application No. 61/660,220, filed on Jun. 15, 2012.

(30) Foreign Application Priority Data

Jun. 15, 2012 (DE) .......................... 10 2012 210 163

(51) Int. Cl.
*C12N 11/08* (2006.01)
*C12N 9/02* (2006.01)
*C12N 11/00* (2006.01)
*C08F 12/08* (2006.01)

(52) U.S. Cl.
CPC .............. *C12N 11/08* (2013.01); *C08F 12/08* (2013.01); *C12N 9/0055* (2013.01); *C12N 9/0061* (2013.01); *C12N 11/00* (2013.01); *C12Y 110/03002* (2013.01); *C12N 2533/00* (2013.01); *C12N 2533/50* (2013.01)

(58) Field of Classification Search
CPC .................................................... C12N 9/0005
See application file for complete search history.

(56) References Cited

FOREIGN PATENT DOCUMENTS

| JP | 2003247174 | * | 5/2003 | ............. C12S 11/00 |
| WO | WO 2008/012236 | | 1/2008 | |

OTHER PUBLICATIONS

Fujisawa, et al. J of Polymer and the Environment, 2001, 9(3):103-108.*
Silva et al. Reactive & Functional Polymers, 2011, 71:713-720.*
Elegir et al. Enzyme and Microbial Technology, 2008, 43:84-92.*
Neifar et al. Letters in Applied Microbiology, 2009, 49:73-78.*
Tong et al. Biotechnol. Prog., 2008, 24:714-719.*
Pich et al., Andrij, "Composite Magnetic Particles as Carriers for Laccase from Trametes versicolor," Macromolecular Bioscience, vol. 6, No. 4, Apr. 12, 2006, pp. 301-310.
Goddard et al., "Polymer surface modification for the attachment of bioactive compounds," Progress in Polymer Science, Pergamon Press, Oxford, GB, vol. 32, No. 7, Jul. 1, 2007.
Szardenings, M., "Enzymatic Treatment Replacing Plasma: Biocompatible Polymer Surfaces," Fraunhofer Institute for Cell Therapy and Immunology IZI, Jan. 1, 2013.

* cited by examiner

*Primary Examiner* — Bin Shen
(74) *Attorney, Agent, or Firm* — Preti Flaherty Beliveau & Pachios LLP (57) ABSTRACT

The invention relates to a method for activating a surface by increasing the hydrophilicity and/or for binding target structures, particularly selected from the group consisting of proteins, cellular proteins, proteins, cells, carbohydrates, peptides and amino acids. It also relates to the use of an oxidoreductase for activating a surface for the mentioned bonds and to corresponding activated surfaces.

29 Claims, 6 Drawing Sheets

METHOD FOR ACTIVATING A SURFACE BY INCREASING THE HYDROPHILICITY AND/OR FOR BINDING TARGET STRUCTURES

The invention relates to a method for activating a surface by increasing the hydrophilicity and/or for binding target structures.

It also relates to the use of an oxidoreductase for activating a surface by increasing the hydrophilicity and/or for the mentioned bonds.

Many polymeric materials are distinguished by a hydrophobic surface. In order to be able to coat, lacquer or glue these materials, a surface activation or modification of these starting materials is essential. Many polymeric materials do not have, for example, the necessary surface characteristics which are required for a long-term stable gluing procedure using adhesives which contain readily volatile organic compounds, or which are required for the production of composite materials.

Furthermore, in the case of microfluidic components, structures need to be purposefully rendered hydrophilic.

In general, surface modifications are significant in areas in which the surface energy of the substrate has to be reduced to improve the wettablity with a liquid substance. Examples of this are polymeric non-woven materials consisting of PE or PP, which are of interest for cotton wool or textiles, for example.

In addition to the technical use, interest is also focussed on the use of plastics materials in biomedical applications. Cell culture dishes are usually produced from polystyrene or polyaliphatic transparent polymers with a very low surface energy which is unsuitable for the settlement of cells.

When working with biological systems and/or molecules, there is a constant demand for materials which are capable of ensuring a local fixing of the structures to be examined. In the case of cells, it is often not only desirable but even necessary that the cells have settled adhesively to a surface to ensure optimum growth/proliferation conditions.

In this respect, it proves to be a challenge where a large number of materials are concerned, particularly also plastics (polymeric materials) to ensure adequate adhesion of the structures to be immobilised. One approach for activating corresponding surfaces is, for example, incubation with acrid oxidising agents, such as chromosulphuric acid. This naturally assumes that the oxidising agent is removed very thoroughly, at least if sensitive molecules/biological structures such as cells are to be immobilised on the corresponding surfaces.

Also, although binding the structures to be examined, particularly cells via antibodies on surfaces is specific to the target structure, it often has an impact on the bound structure and is, moreover, relatively costly.

Hitherto, surfaces have been activated on a large-scale by an electrical pretreatment. Corona and low-pressure plasma treatments are included among the electrical pretreatment methods. In addition to liquid media, gases, for example ozone or fluorine can also be used. A further method provides the thermal pretreatment of a surface, where the surface is melted for a short time and is simultaneously chemically altered (oxidised). A gas flame or a plasma arc is used here as the heat source. There is a risk in methods of this type that toxic compounds will also be produced.

The use of enzyme-based methods has been mentioned previously in a few patent applications (JP2003128835A, US2003017565A, US2010047533A, WO20116041A1). However, these methods differ from the solution described below.

Furthermore, various coating variants are known in the prior art which are to support the binding of structures to be immobilised. Here, at least the additional coating step is time consuming and costly.

In view of the above, the object of the present invention was to provide a method for activating a surface, particularly for binding target structures, in particular biomolecules such as cells and proteins, which method is capable of modifying corresponding surfaces in an economical and reliable manner and under mild conditions.

This object is achieved by a method for activating a surface by increasing the hydrophilicity and/or for binding target structures, selected from the group consisting of proteins, cells, carbohydrates, peptides and amino acids, comprising the step:

The incubation of the surface with an oxidoreductase selected from the group E.C. 1.10 (oxidoreductases which act as donors on diphenols and similar substances) in accordance with the classification according to IntEnz (Integrated relational Enzyme database of the Swiss Institute of Bioinformatics (SIB)) and/or from the group of oxidoreductases which can oxidise substrates without mediator, cofactor and coenzyme.

In the context of this application, the expression "incubation of the surface with an oxidoreductase" is understood as meaning that the surface is brought into contact with the oxidoreductase in a form in which it can usually exercise its enzymatic function. As a general rule, this means that the oxidoreductases are used in solution and in the range of the existing optimum parameters individual to the respective enzyme (for example working temperature, pH value). Within the meaning of the invention, in the pH range, relatively great deviations from the optimum range (based on $K_{max}$) can also be possible.

"In the range of the optimum working temperature" preferably means that the oxidoreductase is used at a temperature of at most 5° C. above an optimum working temperature and at most 15° C. below the optimum working temperature (in each case based on $K_{max}$). Within the meaning of the invention, relatively great deviations from the optimum range based on $K_{max}$ can also be possible in the case of the working temperature.

"Activation of a surface for binding target structures" in this context is understood as meaning that after activation, identical target structures bind to an increasing extent to the activated surface compared to a non-activated surface.

In the present context, "increasing the hydrophilicity" is understood as meaning a reduction in the static wetting angle.

It has surprisingly been found that the mere incubation with corresponding oxidoreductases, particularly laccases, even without cofactor, mediator or coenzyme is capable of activating the surfaces, particularly polymeric surfaces at the interface with an aqueous medium so that a wettablity with water is improved, i.e. the hydrophilicity increases or the wetting angle decreases. The same applies to the binding of target structures, in particular to activate cells and proteins. This presents a large number of advantages:

Incubation with oxidoreductases on the corresponding surfaces can be realised without a great expense in terms of apparatus.

When choosing suitable oxidoreductases, the conditions can be selected such that laborious washing steps are unnecessary.

Also when choosing suitable oxidoreductases, it is possible to allow the target structures to come into contact with the activation solution during the activation step, since the corresponding enzymes do not influence, or at least do not substantially influence the functionality of the target structure.

A large number of oxidoreductases are available, so that depending on the purpose of use, human enzymes for example could also be used.

By the method according to the invention, covalent bonds of the target structure on the surfaces can be ensured and, for example in the case of cells, no negative side effects caused by the bond could be established.

After the binding of the cell structures, the activated surface can be easily deactivated by the addition of protein-containing medium.

All reagents to be used can be stored relatively well.

The reagents used have a low risk potential.

It is possible to provide, in a cost-effective manner, materials for the cell culture, for which the basic material is improved (without activation) for the purpose of use.

It is possible to activate surfaces for a large number of uses, such as adhesion, lacquering and coating applications and to improve the wetting behaviour thereof.

It is possible to improve the usability of microfluidic components by increased hydrophilicity.

Only the uppermost layer of the material surface is modified by the method according to the invention, so that the fundamental material characteristics, particularly the mechanical characteristics are retained even in the case of very thin materials.

Thus, the method according to the invention presents a possibility of activating surfaces for binding target structures, in particular cells and proteins, which method can ensure the activation of surfaces for binding target structures in a relatively simple, economical and rapid manner and optionally in situ.

The oxidoreductase is particularly preferably selected from the group E.C. 1.10.3 (with oxygen as acceptor) and an oxidoreductase is most particularly preferably selected from classes E.C. 1.10.3.2 (laccases) and E.C. 1.14.18.1 (monopherol mono-oxigenase). (The classification was respectively made according to IntEnz, see above, even if the enzymatic activities described here should be ascribed to other classes).

The preferred and particularly preferred oxidoreductases are particularly suited to achieving the advantages mentioned above in a particular manner.

A method according to the invention is preferred in which the incubation takes place without the addition of a compound which comprises a di- or trihydroxyphenyl group.

According to the prior art, it has been necessary hitherto to assume that oxidoreductases, but in particular laccases and/or tyrosinoxidases require hydroxy-substituted phenyl groups in order to catalyse a corresponding oxidation step. Particularly in the case of di- or tri-hydroxyphenyl groups, oxidation produces a (reactive) quinone which can react with the surfaces and thus provides new linking points for the target structures. The fact that a substrate of this type is not required for the activation method according to the invention or is possibly also present on untreated surfaces (for example polystyrene, COC, polypropylene) is a particularly surprising aspect of the present invention.

In this context, it is preferred that no enzyme-specific substrates are added to the oxidoreductases which are used for the method according to the invention.

In the context of this invention, enzyme-specific substrates are substrates which are described in the literature as substrates which are typically converted by this enzyme. Naturally, the surfaces to be activated are not included among the enzyme-specific substrates within the context of this application.

If an additional enzyme-specific substrate is not required for activation of the surfaces, the advantage is provided that fewer chemicals have to be used, the production of the corresponding reaction solutions is easier (and thereby less error-prone) and the reaction system for the activation can be controlled more effectively.

A method in which the incubation takes place without the addition of a redox mediator is preferred according to the invention. Redox mediators (and cofactors or coenzymes) are compounds which support a redox reaction in that they are available as redox partners for the oxidoreductase and/or for the surface to be activated. In the context of this application, oxygen ($O_2$) is to be explicitly not included in the group of redox partners to be added.

According to what has been stated above, it is preferred according to the invention that the method according to the invention is carried out under the influence of oxygen, preferably under the influence of air. The influence of oxygen or air means that the respective gas is freely exchanged with the reaction solution containing the oxidoreductase.

Alternatively, a method according to the invention can be preferred in which the incubation is carried out with the addition of a compound which comprises a di- or trihydroxyphenyl group.

In many cases, the incubation with the addition of a typical substrate, particularly a typical substrate for a laccase or tyrosinoxidase can lead to an improvement in the degree of activation of a surface.

Within the present context, the expression: with the addition "of a typical substrate", in particular of a catechol means that during activation of the surface, the corresponding compound is available in any manner to the enzyme. This can also mean, for example, that the corresponding substrates (or the precursors thereof) have been applied to the corresponding surface and/or optionally have been bound covalently thereto before the addition of the activating oxidoreductase.

An advantage of using catechols (molecules comprising di- or tri-hydroxyphenyl groups) is also seen in the fact that these compounds occur relatively seldom in nature so that the enzyme used for activation does not catalyse any secondary reactions or only catalyses a few secondary reactions.

A method is particularly preferred according to the invention in which incubation takes place with the addition of a compound selected from the group consisting of DOPA, caffeic acid and dopamine.

These substrates are particularly suitable for the activation which is carried out by laccases.

A method according to the invention is preferred in which the material of the surface is selected from the group consisting of plastics, ceramics, glass, carbohydrates and magnetic particles as well as polyacrylic and the derivatives thereof.

Generally preferred, the material of which the surface consists is an optionally modified and/or oxidisable polymeric material.

However, non-polymeric materials can also be preferred for specific purposes of use to activate the surface material.

It is preferred according to the invention that the material of the surface to be activated is selected from the group consisting of polyolefins, polystyrene, polypropylene, polyethylene, polycarbonate, polyacrylic, polymethacrylic, cycloolefins and cycloolefin copolymers and the derivatives thereof and the mixtures thereof.

The preferred surfaces are particularly suitable for the activation within the context of the method according to the invention. In this respect, polystyrene and COC, in particular TOPAS are most particularly preferred.

A method according to the invention is preferred in which the surface is activated in the presence of the target structure.

Thus, it is possible to perform an in situ activation so that laborious addition steps and washing steps are unnecessary.

Preferred incubation times are 20 seconds to 16 hours, more preferably 30 seconds to 12 hours and particularly preferably 1 minute to 3 hours.

Under certain circumstances, a method according to the invention can also be preferred in which the surfaces are incubated with an oxidoreductase solution and the solution is allowed to stand at room temperature until the solvent has completely evaporated.

Particularly good activation results are obtained with this method. In this respect, it is stressed that the oxidoreductase to be used according to the invention is not bound covalently to the surface in the activation method according to the invention.

Thus, a method according to the invention is preferred in which after incubation, the oxidoreductase is completely removed again from the surface. This is preferably carried out during one or more steps.

"To remove completely" in the above context means that it is no longer possible to detect any oxidoreductase on the surface.

It is preferred according to the invention that the oxidoreductase to be used is a laccase, as mentioned, preferably as it occurs in many wood-degrading, in particular lignin-degrading organisms, most particularly *Trametes* spec., most preferably available as laccase C (ASA Spezialchemie, Wolfenbuttel, Germany).

It is preferred that the method according to the invention is carried out so that the static wetting angle is reduced by ≥10.5°, preferably by ≥15°, compared to an untreated surface.

The wetting angle is measured as described in Example 6.

Part of the invention is also the use of an oxidoreductase selected from the group E.C. 1.10 (oxidoreductases which act as donors on diphenols and similar substances) by increasing the hydrophilicity and/or for activating a surface for binding target structures selected from the group consisting of proteins, cellular proteins, cells, carbohydrates, peptides and amino acids.

As stated above, it is particularly surprising that oxidoreductases both with and without a specific substrate to oxidise (mediator/cofactor/coenzyme) are able to activate surfaces.

Another part of the invention is a [ . . . ] for binding target structures, selected from the group consisting of proteins, cells, carbohydrates, peptides and amino acids to an activated surface, which can be produced or is produced according to a method of the invention.

The surfaces or items supporting a surface of this type, which are produced by the method according to the invention have improved binding characteristics for the mentioned target structures. By the method according to the invention, they are easily possible with an economical outlay and without being time-consuming or involving a considerable expense in terms of apparatus.

EXAMPLES

Example 1: Compound Characteristics of Surfaces Treated with Laccase

To investigate the surface modification characteristics of laccase on polystyrene surfaces, a general experimental scheme was used (cf. Table 1). The experiments were carried out at room temperature (20-25° C.).

Experimental Approaches

A "One-pot": laccase, the substrate and BSA were added simultaneously to the surface, incubated for an hour and the supernatant was examined for the BSA concentrations which remained.

B "Activation": laccases and the substrate were introduced into the well/petri dish for 10 minutes, after 10 minutes incubation time, the surface was washed with buffer and BSA was added.

C "Inhibition": like B, before the addition of BSA, ethanol amine was added to block the connection points on the surface. Exposure time: 15 minutes (petri dish) or 30 minutes (well). Thereafter, like B the surface was washed and BSA was added.

D: "Reference": the binding concentration of BSA on a surface which was not treated with laccase was examined (incubation time 60 minutes with the presence of the corresponding substrate).

TABLE 1

| Time [min] | A ("One-pot") | B ("Activation") | C ("Inhibition") | 1 h BSA | D ("Reference") |
|---|---|---|---|---|---|
| 0 | Laccase, BSA, Substrate | Laccase, Substrate | Laccase, Substrate | BSA | Substrate |
| 10 |  | Wash with buffer (pH 7) Addition of BSA | Wash with buffer (pH 7) Addition of ethanol amine |  |  |
| 25 (40) |  |  | Wash with buffer (pH 7) Addition of BSA |  |  |
| 60 | Measurement (Bradford) |  |  | Measurement (Bradford) | Wash with buffer (pH 7) Addition of BSA |

TABLE 1-continued

| Time [min] | A ("One-pot") | B ("Activation") | C ("Inhibition") | 1 h BSA | D ("Reference") |
|---|---|---|---|---|---|
| 70 | | Measurement (Bradford) | | | |
| BS (100) | | | Measurement (Bradford) | | |
| 120 | | | | | Measurement (Bradford) |

TABLE 2

Summary of relevant concentrations:

| Compound | Solvent | Concentration | Volume (Plate/Well) |
|---|---|---|---|
| BSA (Fluka) | Phosphate buffer pH 7 | 1 mg/mL | 1.5 mL (0.1% TWEEN)/ 750 µL |
| Caffeic acid (Carl Roth GmbH) | Phosphate buffer pH 7 | $1.5 \times 10^{-4}$M | 1.5 mL (0.1% TWEEN)/ 750 µL |
| Dopamine (Sigma Aldrich) | Phosphate buffer pH 7 | $1.5 \times 10^{-4}$M | 1.5 mL (0.1% TWEEN)/ 750 µL |
| L-Dopa (Sigma Aldrich) | Phosphate buffer pH 7 10 mM | $1.5 \times 10^{-4}$M | 1.5 mL (0.1% TWEEN)/ 750 µL |
| Ethanol amine (Sigma Aldrich) | Water | 0.1M | 1.5 mL (0.1% TWEEN)/ 25 µL |
| Laccase (ASA Spezialchemie GmbH) | Phosphate buffer pH 7 10 mM | 20 mg/mL | |

The protein concentration was determined according to Bradford, for this the supernatants were stated according to Table 1, were collected [ . . . ] time and 250 µl of each sample were added to 1 ml of Bradford reagent. For the 1 pot experiment, the ratio was adapted, here 500 µl were added to 750 µl of Bradford reagent. 50 µl of the respectively resulting solution were dissolved in 950 µl of buffer and the concentration was then determined in a semi-micro cuvette at 595 nm.

960 mm petri dishes (Greiner) were examined.

Figure 1:
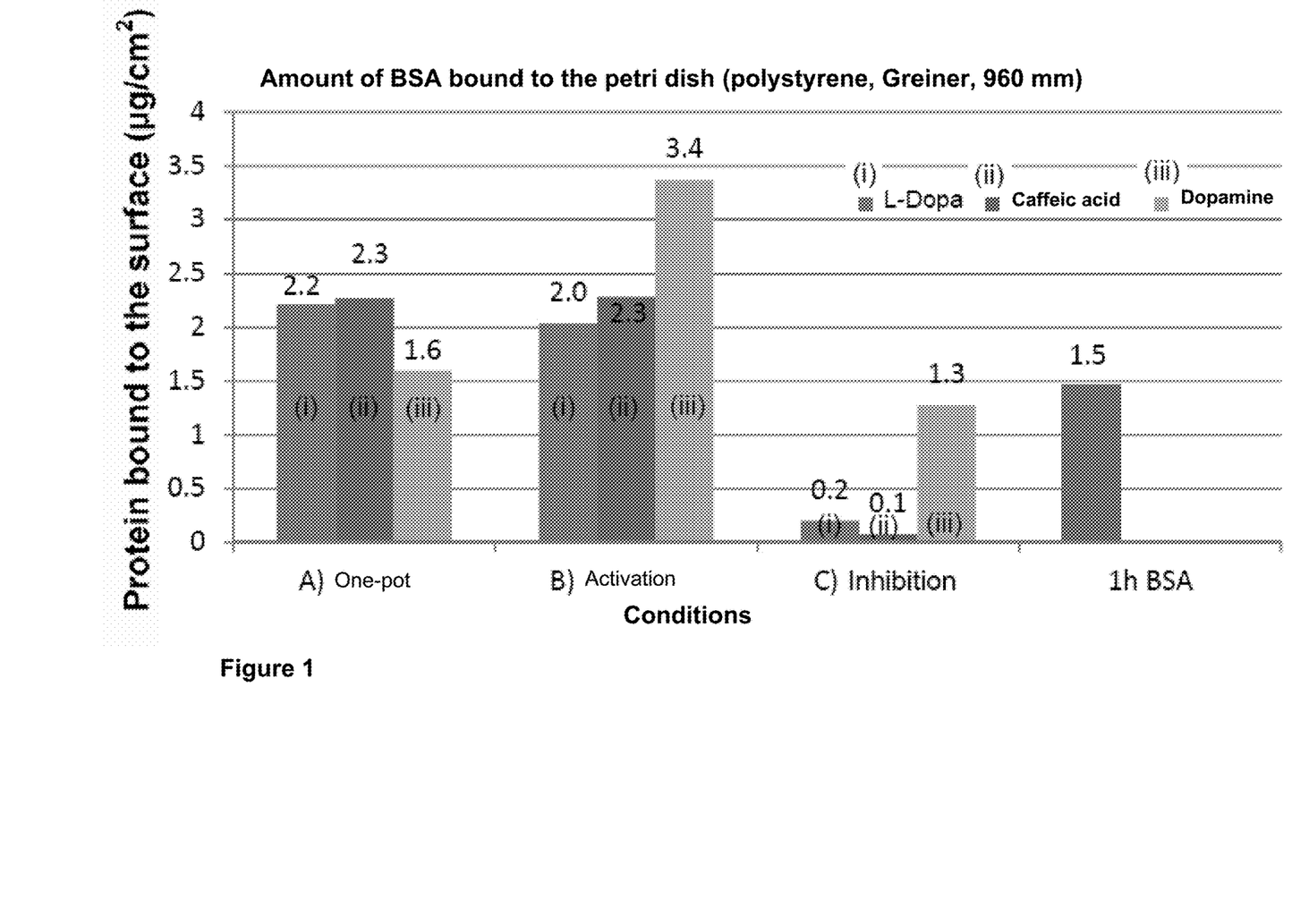

FIG. 1 shows the amount of BSA which was bound after incubation for one hour (determined by forming the difference for the total protein content of the supernatant and after the incubation time). It is found that the BSA binding capacity of the modified polystyrene surfaces increased in every case, sometimes by more than factor 2, compared to the right-hand column which shows the amount of BSA which binds to the non-activated polystyrene surface. In this respect, the activation is shown for all three tested substrates, namely caffeic acid, L-dopa and dopamine.

Example 2

This experiment was to determine whether the effect observed in Example 1 can also be observed for another polystyrene surface. In this case, Falcon 240 mm 6 well plates for cell cultures were used, i.e. this is a surface which had already been steel-treated. The experimental scheme described in Example 1 was used.

Figure 2:
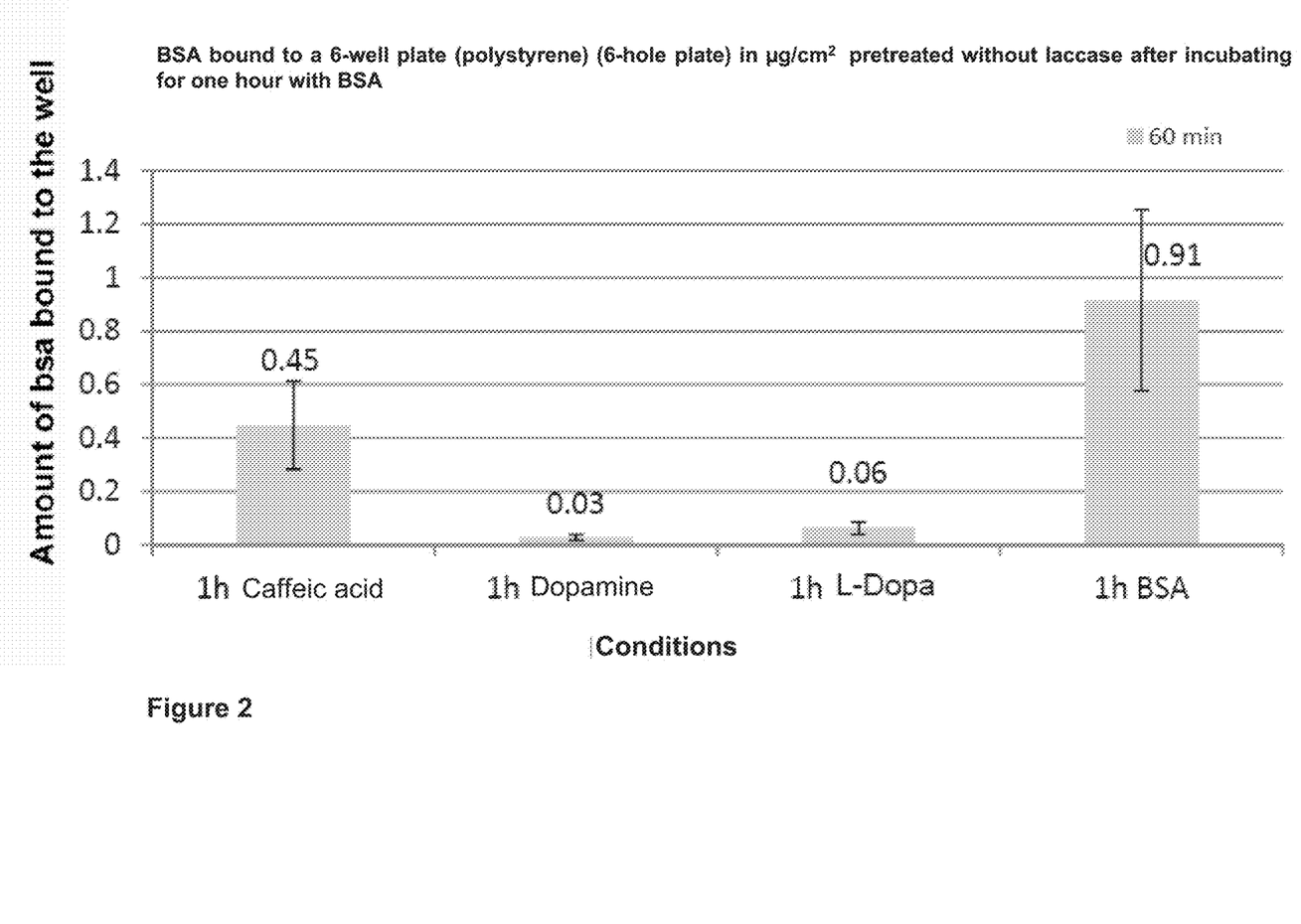

FIG. 2 shows the results of a pretreatment with the respective substrate without laccase.

Figure 3:
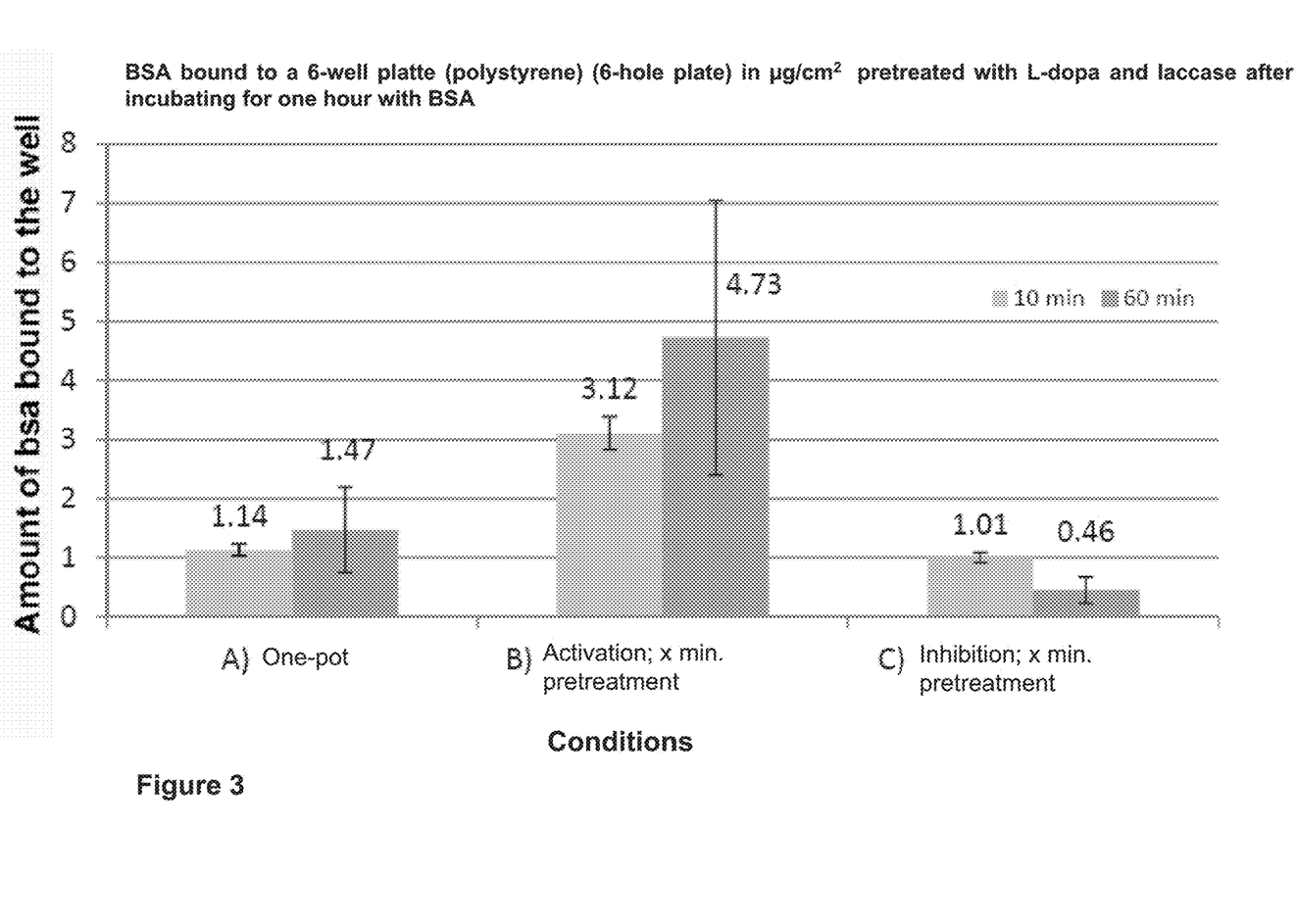

FIG. 3 shows the results of a pretreatment with laccase and L-dopa.

Figure 4:
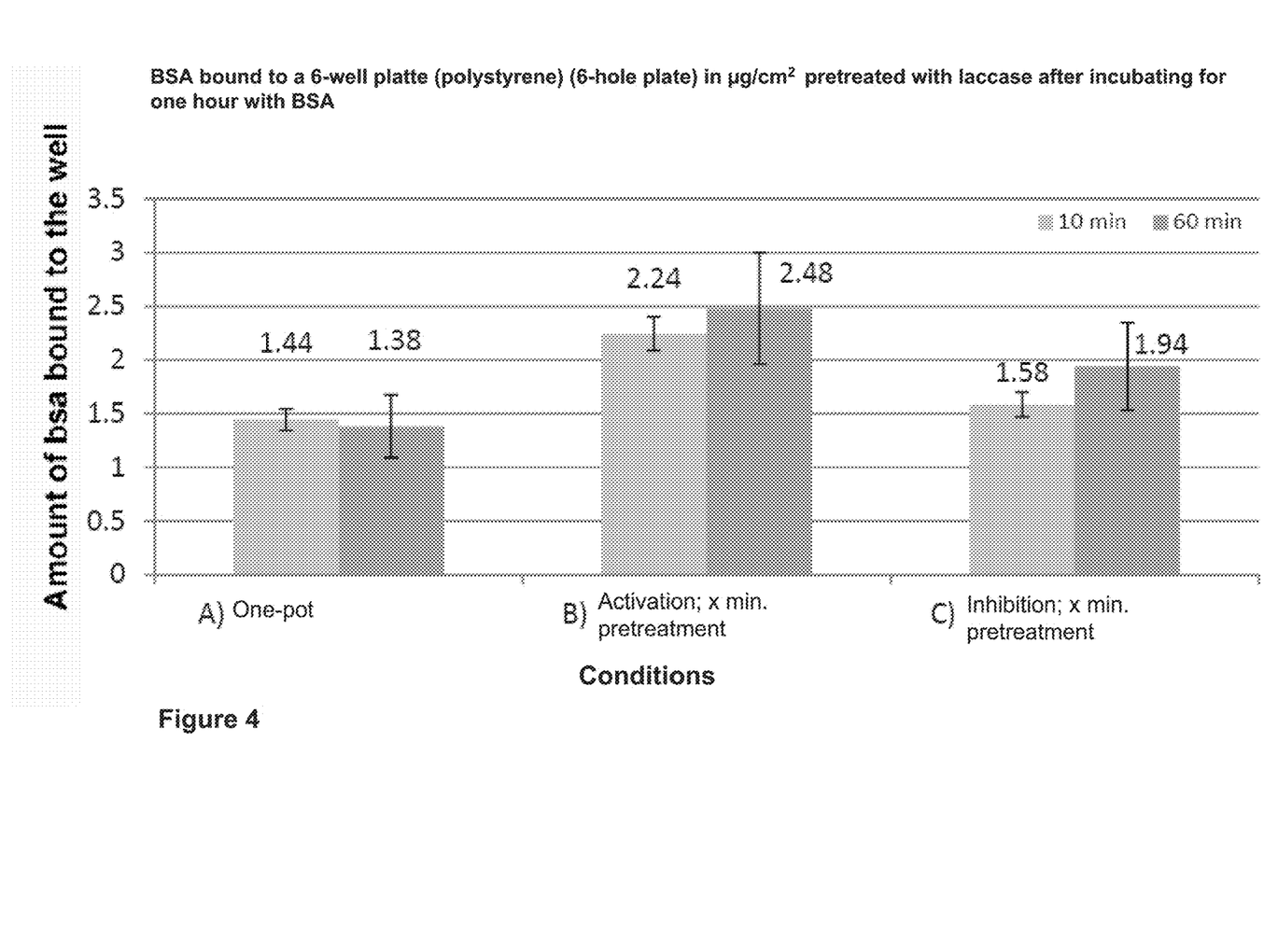

FIG. 4 shows the results of a pretreatment with laccase alone.

Figure 5:
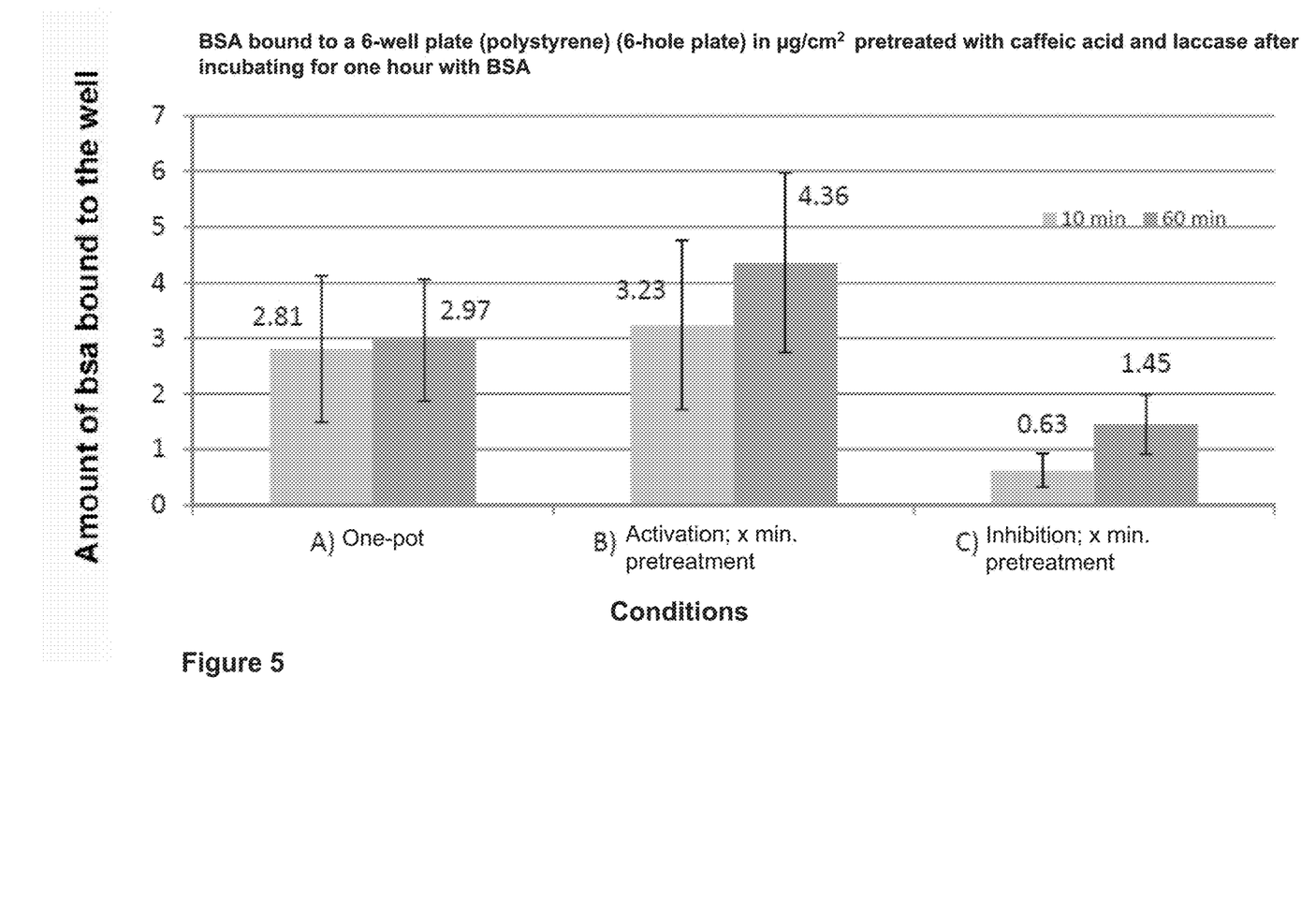

FIG. 5 shows the results of a pretreatment with laccase and caffeic acid.

Figure 6:
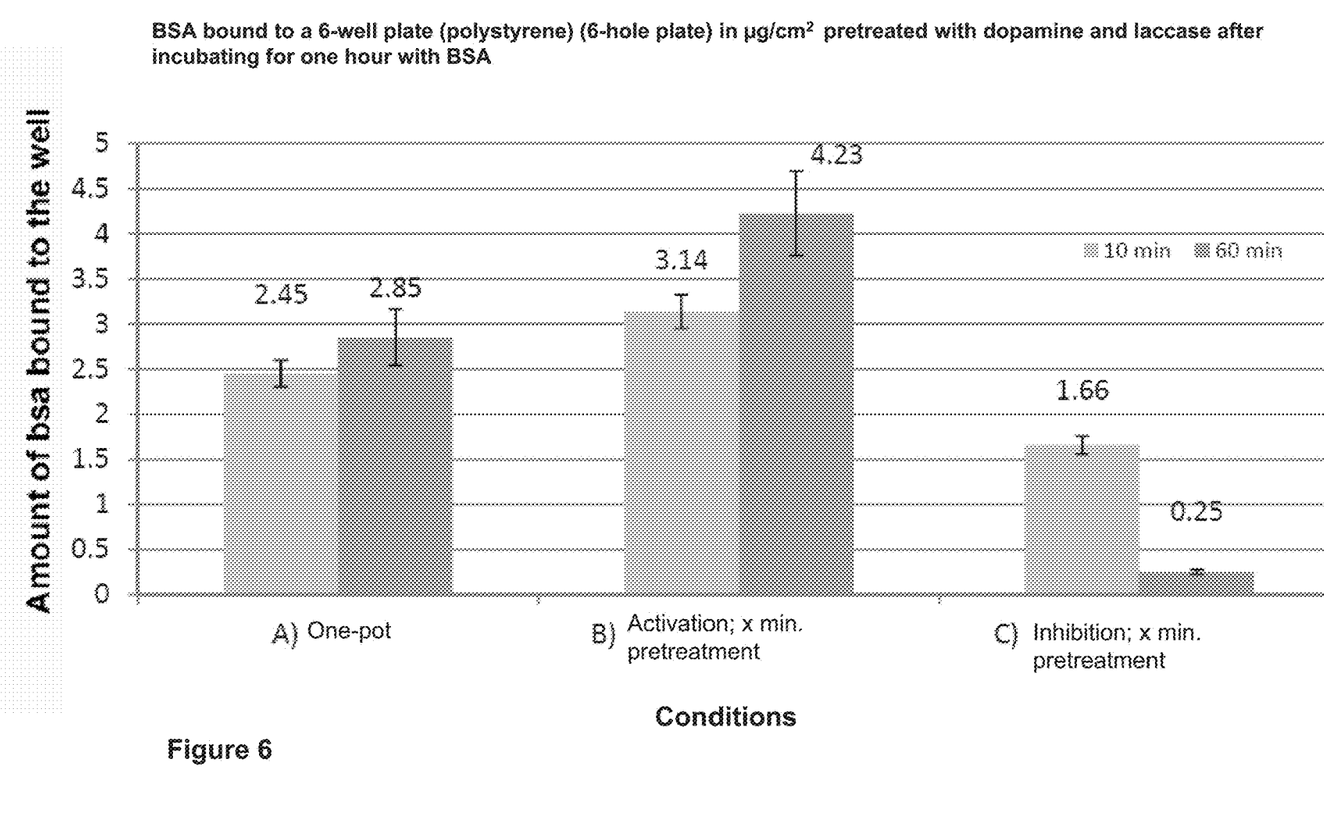

FIG. 6 shows the results of a pretreatment with laccase and dopamine.

FIG. 2 shows that a pretreatment using the respective substrate does not result in an increase in the BSA binding capacity of the treated surfaces if the treatment did not also contain a treatment with laccase.

FIG. 3 shows, inter alia, that an activation with laccase combined with L-dopa results in an activation, said activation increasing as the pretreatment duration increases and it results in an improved binding capacity.

FIG. 4 shows that an effective activation is also possible as long as the pretreatment is only carried out with laccase, without a further substrate.

FIG. 5 shows the effects of a pretreatment of laccase with caffeic acid, where analogously to the previously described figures, an increase in binding capacity could be respectively observed. However, it bears mentioning in this connection that caffeic acid does not contain an amino group, so that it can be assumed that the actual activation mechanism is independent of this group.

FIG. 6 shows the corresponding results with dopamine as an alternative substrate for laccase in the pretreatment. Here as well, an analogous increase in binding capacity can be observed.

Example 3: Binding Experiments with Cells

Cells of cell line HaCaT P14 were introduced onto 160 mm polystyrene cell suspension culture plates which had been pretreated analogously to Example 2.

Here as well, it was possible to see a significant increase in the adhesion capacity of the plates analogously to Examples 1 and 2. Even better results could be achieved by allowing the respective pretreatment solution (incubation solution) to dry in overnight and by subsequently carrying out the cell adhesion experiments.

Example 4: Activation of Petri Dishes Consisting of TOPAS

Petri dishes consisting of TOPAS (COC polymer) by ibidi, Martinsried (µ-dish) were used as follows:
1. ibidi µ-dish, untreated: normal hydrophobic vessels
2. ibidi µ-dish, ibidi treat: commercially available with plasma-treated surface
3. ibidi µ-dish, treated according to the invention with 0.5 U laccase in 2 ml in 10 mmol phosphate powder, pH 7.0 (exposure time 20 minutes)
4. ibidi µ-dish, treated according to the invention with 0.1 U laccase in 2 ml in 10 mmol phosphate powder, pH 7.0 (exposure time 60 minutes)

After the exposure time, the plates were washed with deionised water and dried with nitrogen. Upon applying a drop of water, it was found that samples 3 and 4 (according to the invention), compared to the untreated sample (sample 1) exhibited a spread of the drop which was significantly greater and was even comparable with the plasma-treated sample (sample 2). In the case of sample 3 according to the invention, changes in the surface tension were observed even after 5-10 minutes, XPS Results The quantitative evaluation of the XPS overview spectra for the investigated samples produces the following tabulated elemental chemical compositions of the near-surface area of the analysed sites (cf. Table 1). The concentrations of the detected elements, with the exception of hydrogen and helium, are stated as atomic percentages (at %).

TABLE 1

XPS investigation on the following samples, chemical compositions of the surfaces in atomic percent (at %):

|  | C (at %) | O (at %) | N (at %) | Si (at %) | P (at %) | Ca (at %) | S (at %) | Na (at %) | F (at %) | Mg (at %) |
|---|---|---|---|---|---|---|---|---|---|---|
| Plate 1: Untreated plate with Ac buffer | 96.2 | 3.1 | 0.1 | <0.1 | <0.1 | 0.1 | 0.3 | — | — | — |
| Plate 2: Plasma-treated plate with Ac buffer | 83.0 | 13.6 | 0.7 | 1.3 | — | 0.4 | — | 0.8 | 0.2 | 0.1 |
| Plate 3: Untreated plate + Laccase + Ac buffer | 83.3 | 10.4 | 5.0 | 0.4 | <0.1 | 0.1 | 0.1 | 0.2 | 0.4 | <0.1 | while in the case of sample 4 according to the invention, these changes appeared after between 15 and 45 minutes.

Example 5: Surface Investigation Using X-Ray Photoelectron Spectroscopy (XPS)

X-Ray Photoelectron Spectroscopy (XPS)

Measuring principle: X-ray photoelectron spectroscopy (XPS) is based on the external photo effect in which photoelectrons are released from the surface of a solid body by X-ray radiation. The determination of the kinetic energy of these electrons allows conclusions to be drawn about the chemical composition and the electronic nature of the investigated sample surface. The analysis is surface-sensitive. The associated depth of information which is determined by the restricted emergence depth of the emitted electrons is approximately 10 nm. The method allows a quantitative determination of the chemical composition of the area close to the surface. In this respect, all elements except for hydrogen and helium were detected. The detection sensitivity of the method is element-specific and is approximately 0.1 at %, i.e. approximately 1000 ppm. To compensate for charging effects, the C1s main photo line is fixed at 285 eV during the evaluation, consequently the positions of further photo lines are shifted accordingly.

Measuring parameter: the XPS investigations were carried out using a Thermo K-Alpha K1102 system with a nitrogen glove box connected upstream for handling air-sensitive samples. Parameter: measurement angle of the photoelectrons 0° monochromatised AlKα-excitation, constant analyser energy mode (CAE) with 150 eV passing energy in overview spectra and 20 eV in energetically high-resolution line spectra, analysis surface: 0.40 mm. Electrically non-conductive samples are neutralised by a combination of low-energy electrons and low-energy argon ions.

Plates 1 and 2 are the same material as plates 1 and 2 from Example 4. Plate 3 is the same material as plate 1. All three plates were incubated in respectively 4 ml acetate buffer (2 mol/l, pH=4.7) for 15 hours, and plate 3 (according to the invention) contained incubation solution (4 U laccase in 4 ml acetate buffer).

As a result, it is found that with the method according to the invention, it is possible to incorporate an appreciable amount of oxygen in the surface. It is also found that additional nitrogen is also incorporated. Consequently, surfaces produced according to the invention are preferred which have a nitrogen content of 3% based on the total number of atoms which can be determined on the surface by XPS (without H).

Example 6: Determination of Wetting Angle

The samples were prepared as follows: before the start of the treatment, the samples were wiped clean with isopropanol and the clean substrates were left for 15 minutes under a hood to remove any remaining traces of isopropanol. The substrates were then placed for 3 h in respectively 50 ml of a solution of a) laccase in 0.1M phosphate buffer (0.5 U/ml), b) denatured laccase in 0.1M phosphate buffer (starting concentration before denaturation 0.5 U/ml) and c) demineralised water. After being removed from storage, the respective substrates were each washed in 50 ml of demineralised water and dried in a stream of nitrogen.

Thereafter, the static contact angle with water was determined according to DIN 55660-2 (December 2011).

The results are summarised in Table 2:

| Sample | | Contact angle [°] | | |
|---|---|---|---|---|
| PS | -H | 91.4 | 91.0 | 93.5 |
| | -L | 72.2 | 72.6 | 68.2 |

-continued

| Sample | | Contact angle [°] | | |
|---|---|---|---|---|
| PE | -D | 81.2 | 84.9 | 84.3 |
| | -H | 94.0 | 95.3 | 92.2 |
| | -L | 83.1 | 83.4 | 81.3 |
| | -D | 93.8 | 88.6 | 92.0 |
| PC | -H | 90.4 | 90.4 | 89.0 |
| | -L | 61.3 | 60.2 | 59.9 |
| | -D | 82.1 | 82.3 | 86.6 |

Legend:
-H water (reference)
-L laccase treatment
-D denatured laccase

For denaturation, laccase was heated until dry at 90° C. in 50 ml of demineralised water.

The remaining solids were then taken up in 50 ml of phosphate buffer and used in the appropriate experiments.

As a result, it is found that a significant reduction of the water contact angle (wetting angle) is possible with the treatment according to the invention of the corresponding surfaces.

The invention claimed is:

1. Method for activating a surface comprising:
   incubating the surface with an oxidoreductase selected from the group E.C. 1.10 including oxidoreductases which act as donors on diphenols and similar substances in accordance with the classification according to the Integrated relational Enzyme database of the Swiss Institute of Bioinformatics thereby forming an activated surface;
   wherein the incubating step does not comprise adding to the surface a redox mediator;
   wherein the surface comprises a material selected from the group consisting of a plastic, a ceramic, and a magnetic particle; and
   wherein the incubating step comprises contacting the surface with the oxidoreductase in a form in which the oxidoreductase can exercise enzymatic function; and
   after the incubating step, binding a target structure other than the oxidoreductase to the activated surface;
   wherein the target structure is selected from the group consisting of a protein, a cellular protein, a cell, a peptide, and an amino acid.

2. Method according to claim 1, wherein the incubating step is carried out without the addition of a compound which comprises a di- or tri-hydroxyphenyl group.

3. Method according to claim 1, wherein the incubating step comprises adding to the surface a compound comprising a di- or tri-hydroxyphenyl group.

4. Method according to claim 3, wherein the incubating step comprises adding to the surface the compound selected from the group consisting of a DOPA, a caffeic acid and a dopamine.

5. Method according to claim 1, wherein the surface comprises a material selected from the group consisting of a polyolefin, a polystyrene, a polypropylene, a polyethylene, a polycarbonate, a polyacrylic, a polymethacrylic, a cycloolefin copolymer, a derivative thereof, and a mixture thereof.

6. Method according to claim 1, wherein the incubating step comprises incubating the surface with the oxidoreductase in a solvent in a solution and maintaining the solution at a room temperature until the solvent has completely evaporated.

7. Method according to claim 1, wherein after the incubating step, the oxidoreductase is not detectable on the surface.

8. Method according to claim 1, wherein the oxidoreductase is a laccase.

9. Method according to claim 1, wherein
   the incubating step comprises adding to the surface a compound which comprises a di- or tri-hydroxyphenyl group selected from the group consisting of a DOPA, a caffeic acid and a dopamine;
   the surface comprises the material selected from the group consisting of a polyolefin, a polystyrene, a polypropylene, a polyethylene, a polycarbonate, a polyacrylic, a polymethacrylic, a cycloolefin copolymer, a derivative thereof, and a mixture thereof;
   the incubating step comprises incubating the surface with a solution of the oxidoreductase and a solvent and maintaining the solution at a room temperature until the solvent has completely evaporated;
   after the incubating step, the oxidoreductase is not detectable on the surface; and
   the oxidoreductase is a laccase.

10. The method of claim 1, wherein the incubating step is conducted during an incubation time in a range of 20 seconds to 16 hours.

11. The method of claim 1, wherein the oxidoreductase is in a solvent in a solution having a pH and a working temperature selected for optimization of enzymatic function of the oxidoreductase.

12. Method of using an oxidoreductase comprising:
    selecting the oxidoreductase from the group E.C. 1.10 including oxidoreductases which act as donors on diphenols and similar substances in accordance with the classification according to the Integrated relational Enzyme database of the Swiss Institute of Bioinformatics;
    incubating a surface with the oxidoreductase comprising contacting the surface with the oxidoreductase in a form in which the oxidoreductase can exercise enzymatic function; and
    binding to the activated surface a target structure other than the oxidoreductase;
    wherein the target structure is selected from the group consisting of a protein, a cellular protein, a cell, a carbohydrate, a peptide, and an amino acid;
    wherein the incubating step does not comprise adding to the surface a redox mediator; and
    wherein the surface comprises a material selected from the group consisting of a plastic, a ceramic, and a magnetic particle.

13. Method according to claim 12, wherein the incubating step does not comprise adding to the surface a compound containing a di-hydroxyphenyl group or tri-hydroxyphenyl group.

14. The method of claim 12, wherein the surface has initially a first hydrophilicity and a first static wetting angle, and the activated surface has a second hydrophilicity being increased relative to the first hydrophilicity and a second static wetting angle being decreased relative to the first static wetting angle.

15. The method of claim 14, wherein the second static wetting angle is decreased relative to the first static wetting angle by $\geq 10.5°$.

16. The method of claim 12, wherein the incubating step is conducted during an incubation time in a range of 20 seconds to 16 hours.

17. The method of claim 12, wherein the oxidoreductase is in a solvent in a solution having a pH and a working temperature selected for optimization of enzymatic function of the oxidoreductase.

18. Method for activating a surface comprising:
    incubating the surface with an oxidoreductase selected from the group E.C. 1.10 including oxidoreductases which act as donors on diphenols and similar substances in accordance with the classification according to the Integrated relational Enzyme database of the Swiss Institute of Bioinformatics thereby forming an activated surface activated for binding of a target structure other than the oxidoreductase and selected from the group consisting of a protein, a cell, a peptide, and an amino acid;

wherein the incubating step comprises contacting the surface with the oxidoreductase in a form in which the oxidoreductase can exercise enzymatic function, the oxidoreductase being in a solvent in a solution;

maintaining the solution at a room temperature until the solvent has completely evaporated; and after the incubating step, binding the target structure to the activated surface.

19. The method of claim 18, wherein the incubating step is conducted during an incubation time in a range of 20 seconds to 16 hours.

20. The method of claim 18, wherein the solution has a pH selected for optimization of enzymatic function of the oxidoreductase.

21. Method for activating a surface comprising:
incubating the surface with an oxidoreductase selected from the group E.C. 1.10 including oxidoreductases which act as donors on diphenols and similar substances in accordance with the classification according to the Integrated relational Enzyme database of the Swiss Institute of Bioinformatics thereby activating the surface;

wherein the incubating step does not comprise adding to the surface a redox mediator;

wherein the surface comprises a material selected from the group consisting of a plastic, a ceramic, and a magnetic particle;

wherein the incubating step comprises contacting the surface with the oxidoreductase in a form in which the oxidoreductase can exercise enzymatic function; and wherein prior to the incubating step, the surface has a first hydrophilicity and a first static wetting angle and after the incubating step, the surface has a second hydrophilicity increased relative to the first hydrophilicity and a second static wetting angle decreased relative to the first static wetting angle; and after the incubating step, binding a target structure other than the oxidoreductase to the activated surface;

wherein the target structure is selected from the group consisting of a protein, a cellular protein, a cell, a carbohydrate, a peptide, and an amino acid.

22. The method of claim 21, wherein the second static wetting angle is decreased relative to the first static wetting angle by ≥10.5°.

23. Method for activating a surface comprising:
incubating the surface with an oxidoreductase selected from the group E.C. 1.10 including oxidoreductases which act as donors on diphenols and similar substances in accordance with the classification according to the Integrated relational Enzyme database of the Swiss Institute of Bioinformatics for an incubation time period thereby forming an activated surface;

wherein the incubating step does not comprise adding to the surface a redox mediator;

wherein the surface comprises a material selected from the group consisting of a plastic, a ceramic, and a magnetic particle; and wherein the incubating step comprises contacting the surface with the oxidoreductase in a form in which the oxidoreductase can exercise enzymatic function; and wherein after the incubating step, a target structure other than the oxidoreductase and selected from the group consisting of a protein, a cell, a peptide, and an amino acid binds to an increasing extent to the surface as compared to a non-activated surface.

24. The method of claim 23, wherein the incubation time period is in a range of 20 seconds to 16 hours.

25. Method of using an oxidoreductase comprising:
selecting the oxidoreductase from the group E.C. 1.10 including oxidoreductases which act as donors on diphenols and similar substances in accordance with the classification according to the Integrated relational Enzyme database of the Swiss Institute of Bioinformatics; and incubating a surface with the oxidoreductase comprising contacting the surface with the oxidoreductase in a form in which the oxidoreductase can exercise enzymatic function for an incubation time period for activating the surface after the incubating step;

binding a target structure other than the oxidoreductase and selected from the group consisting of a protein, a cellular protein, a cell, a carbohydrate, a peptide, and an amino acid;

wherein the target structure binds to the activated surface to an increasing extent as compared to a non-activated surface;

wherein the incubating step does not comprise adding to the surface a redox mediator; and wherein the surface comprises a material selected from the group consisting of a plastic, a ceramic, and a magnetic particle.

26. The method of claim 25, wherein the incubation time period is in a range of 20 seconds to 16 hours.

27. The method of claim 25, wherein before the incubating step, the surface has a first hydrophilicity and a first static wetting angle, and after the incubating step, the surface has a second hydrophilicity being increased relative to the first hydrophilicity and a second static wetting angle being decreased relative to the first static wetting angle.

28. Method for activating a surface comprising:
incubating the surface with an oxidoreductase selected from the group E.C. 1.10 including oxidoreductases which act as donors on diphenols and similar substances in accordance with the classification according to the Integrated relational Enzyme database of the Swiss Institute of Bioinformatics for an incubation time period for activating the surface such that after the incubating step, a target structure other than the oxidoreductase and selected from the group consisting of a protein, a cell, a peptide and an amino acid binds to the surface to an increasing extent as compared to a non-activated surface;

wherein the incubating step comprises contacting the surface with the oxidoreductase in a form in which the oxidoreductase can exercise enzymatic function, the oxidoreductase being in a solvent in a solution; and maintaining the solution at a room temperature until the solvent has completely evaporated.

29. The method of claim 28, wherein the incubation time period is in a range of 20 seconds to 16 hours.

* * * * *